(12) United States Patent
Johnson et al.

(10) Patent No.: US 6,527,810 B2
(45) Date of Patent: *Mar. 4, 2003

(54) BONE SUBSTITUTES

(75) Inventors: James R. Johnson, Boca Raton, FL (US); Jeffrey G. Marx, Menomonie, WI (US); Wesley D. Johnson, Menomonie, WI (US)

(73) Assignee: Wright Medical Technology, Inc., Arlington, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/740,807

(22) Filed: Dec. 21, 2000

(65) Prior Publication Data

US 2001/0053937 A1 Dec. 20, 2001

Related U.S. Application Data

(62) Division of application No. 08/944,006, filed on Oct. 1, 1997, now Pat. No. 6,296,667.

(51) Int. Cl.⁷ .................................................. A61F 2/28
(52) U.S. Cl. ................. 623/23.56; 623/23.51; 623/23.53; 623/23.61; 424/423; 424/426
(58) Field of Search .............. 623/901, 16.11, 623/20.17, 23.51, 23.53, 23.54, 23.56, 23.59, 23.61, 23.63; 424/422, 423, 424, 425, 426

(56) References Cited

U.S. PATENT DOCUMENTS

| | | |
|---|---|---|
| 3,090,094 A | 5/1963 | Schwartzwalder et al. |
| 3,662,405 A | 5/1972 | Bortz et al. |
| 3,905,047 A | 9/1975 | Long |
| 4,000,525 A | 1/1977 | Klawitter et al. |
| 4,168,326 A | 9/1979 | Broemer et al. |
| 4,222,128 A | 9/1980 | Tomonaga et al. |
| 4,237,559 A | 12/1980 | Borom |
| 4,343,704 A | 8/1982 | Brockmeyer |
| 4,365,356 A | 12/1982 | Broemer et al. |
| 4,371,484 A | 2/1983 | Inukai et al. |
| 4,596,574 A | 6/1986 | Urist |
| 4,599,085 A | 7/1986 | Riess et al. |
| 4,626,392 A | 12/1986 | Kondo et al. |

(List continued on next page.)

FOREIGN PATENT DOCUMENTS

| | | |
|---|---|---|
| DE | 19610715 | 6/1997 |
| EP | 0299342 | 1/1989 |
| EP | 0 335 359 | 10/1989 |
| EP | 0585978 | 3/1994 |
| EP | 0714666 | 6/1996 |
| JP | 4-15062 | 1/1992 |
| WO | 95/28973 | 11/1995 |
| WO | 01/12106 | 2/2001 |

OTHER PUBLICATIONS

Aksaci, D., et al., "Porous Fluorapatite/Spinel Osteoceramic For Bone Bridges", *Phosphorus: Studies in Inorganic Chemistry*, vol. 6:283–301, ( 1985 ).

McGee, et al., "General Requirements for A Successful Orthopedic Implant", pp. 69–82.

(List continued on next page.)

*Primary Examiner*—Corrine McDermott
*Assistant Examiner*—Cheryl L. Miller

(57) ABSTRACT

A strong, porous article useful as a bone substitute material. The article comprises a continuous strong framework structure having struts defining interstices which interconnect throughout the bulk volume, and may have ceramic or osteoconductive material occupying at least a portion of the same bulk volume as the framework structure. Either as a coating on the strong framework struts or between the framework struts and the ceramic or osteoconductive-osteoinductive materials is a resilient material which serves to distribute stresses within the article.

36 Claims, 5 Drawing Sheets

U.S. PATENT DOCUMENTS

| | | |
|---|---|---|
| 4,629,464 A | 12/1986 | Takata et al. |
| 4,722,870 A | 2/1988 | White |
| 4,878,914 A | 11/1989 | Miwa et al. |
| 4,950,294 A | 8/1990 | Hakamatsuka |
| 4,957,509 A | 9/1990 | Tamari et al. |
| 4,960,426 A | 10/1990 | Atsumi |
| 4,976,736 A | 12/1990 | White et al. |
| 4,983,182 A | 1/1991 | Kijima et al. |
| 5,001,169 A | 3/1991 | Nathan et al. |
| 5,007,930 A | 4/1991 | Dorman et al. |
| 5,037,438 A | 8/1991 | Davidson |
| 5,084,051 A | 1/1992 | Tormala et al. |
| 5,141,510 A | 8/1992 | Takagi et al. |
| 5,152,791 A | 10/1992 | Hakamatsuka et al. |
| 5,171,720 A | 12/1992 | Kawakami |
| 5,185,177 A | 2/1993 | Kijima et al. |
| 5,192,325 A | 3/1993 | Kijima et al. |
| 5,205,921 A | 4/1993 | Shirkanzadeh |
| 5,211,664 A | 5/1993 | Tepic et al. |
| 5,231,169 A | 7/1993 | Constantz et al. |
| 5,273,964 A | 12/1993 | Lemons |
| 5,282,861 A | 2/1994 | Kaplan |
| 5,314,478 A | 5/1994 | Oka et al. |
| 5,356,436 A | 10/1994 | Nonami et al. |
| 5,366,508 A | 11/1994 | Brekke |
| 5,397,362 A | 3/1995 | Noda |
| 5,458,643 A | 10/1995 | Oka et al. |
| 5,464,440 A | 11/1995 | Johansson |
| 5,522,894 A | 6/1996 | Draenert |
| 5,531,794 A | 7/1996 | Takagi et al. |
| 5,549,123 A | 8/1996 | Okuyama et al. |
| 5,549,685 A | 8/1996 | Hayes |
| 5,624,674 A | 4/1997 | Seare, Jr. |
| 5,626,861 A | 5/1997 | Laurencin et al. |
| 5,629,186 A | 5/1997 | Yasukawa et al. |
| 5,645,593 A | 7/1997 | Woods et al. |
| 5,676,699 A | 10/1997 | Gogolewski et al. |
| 5,681,572 A | 10/1997 | Seare, Jr. |
| 5,702,449 A | 12/1997 | McKay |
| 5,716,414 A | 2/1998 | Caldarise |
| 5,725,813 A | 3/1998 | Nies |
| 5,769,897 A | 6/1998 | Harle |
| 5,776,193 A | 7/1998 | Kwan et al. |
| 5,783,248 A | 7/1998 | Lin et al. |
| 5,830,493 A | 11/1998 | Yokota et al. |
| 5,876,446 A | 3/1999 | Agrawal et al. |
| 5,899,939 A | 5/1999 | Boyce et al. |
| 5,972,368 A | 10/1999 | McKay |
| 6,010,336 A | 1/2000 | Shimotoso et al. |
| 6,037,519 A | 3/2000 | McKay |
| 6,039,762 A | 3/2000 | McKay |
| 6,123,731 A | 9/2000 | Boyce et al. |
| 6,214,049 B1 | 4/2001 | Gayer et al. |
| 6,261,586 B1 | 7/2001 | McKay |
| 6,302,913 B1 | 10/2001 | Ripamonti et al. |
| 6,312,472 B1 | 11/2001 | Hall et al. |
| 6,340,648 B1 | 1/2002 | Imura et al. |
| 6,346,123 B1 | 2/2002 | McKay |
| 6,376,573 B1 * | 4/2002 | White et al. ............... 523/115 |
| 2001/0018614 A1 | 8/2001 | Bianchi |

OTHER PUBLICATIONS

Ito, Kuniomi, et al., "Osteogenic Activity of Synthetic Hydroxylapatite With Controlled Texture–on The Relationship Of Osteogenic Quanity t. . . ", *CRC Handbook Of Bioactive Ceramics*, vol. 11:39–44.

Johnson, Kenneth D. et al., "Porous Ceramics As Bone Graft Substitutes In Long Bone Defects . . . ", *J. Orthop. Rev.*, vol. 14(13):351–369, (1996).

"Bone Grafts And Bone Substitutes", *Orthopedic Network News*, vol. 6(4):7–9, (1995).

Constantz, Brent R., et al., "Skeletal Repair By In Situ Formation Of The Mineral Phase Of Bone", *Science*, vol. 267dd: 1796–1799, (1995).

Chaki T.K. et al., "Strengthening Behavior Of Hydroxyapatite–Silver Composite", *Bioceramics: Materials And Applications*, pp. 235–244.

Damien, C. et al., "Bone Graft and Bone Graft Substitutes: A Review Of Current Technology and Applications", *J. App. Biomat.*, vol. 2:187–208, (1991).

Ioku, Koji, et al., "Dense/Porous Layered Apatite Ceramics Prepared By HIP Post–Sintering", *J. Mat. Science*, pp. 1203–1204, (1989).

Wu, Jenn–Ming, et al., "Sintering Of Hydrowylapatite–Zirconia Composite Materials", *J. Science*, pp. 3771–3777, (1988).

Li J., et al., "High–Strength Biofunctional Zirconia: Mechanical Properties and Static Fatigue Behavior Of Zirconia–Apatite Composites", *J. Bio. Sci. Mat.*, pp. 50–54, (1993).

Suda, Akio, et al., "Biocompatibility Of Zirconia Dispersed Hydroxyaptite Ceramics", *J. Jap. Orthop. Assoc.*, vol. 64:249–258.

Takaoka, Kunio, et al., "Ectopic Bone Induction On And In Porous Hydroxyapatite Combined With Collagen And Bone Morphogenetic Protein", *Clinical Orthopedics*, No. 234:250–254, (1988).

Mattioli–Belmonte, et al., "Osteoinduction In The Presence Of Chitosan–Coated Porous Hydroxyapatite", *J. Bio. Comp. Poly.*, vol. 10:249–257, (1995).

Wan, Andrew, et al., "Hydroxyapatite Modified Chitin As Potential Hard Tissue Substitute Material", *J. Bio. Mat. Res.*, vol. 38(3):235–241, (1997).

Zhang, Qi–Qing, "Porous Hydroxyapatite Reinforced With Collagen Protein", *Marcel Dekker, Inc.*, pp. 693–702, (1996).

Gao, T., et al., "Enhanced Healing Of Segmental Tibial Defects In Sheep By A Composite Bone Substitute Composed of Traicalcium Phosphate Cylinder, Bone . . . ", *J. Bio. Mat. Res.*, vol. 32:505–512, (1996).

Verheyen, et la., "Hydroxylapatite/Poly (L–Lactide) Composites: An Animal Study On Push–out Strengths And Interface Histology", *J. Bio. Mat. Res.*, vol. 27:433–444, (1993).

Tenhuisen, K. et al., "Formation And Propertied Of A Synthetic Bone Composite: Hydroxyapatite–Collagen", *J. Bio. Mat. Res.*, vol. 29:803–810, (1995).

Muller–Mai, C. et al., "Nanoapatite And Organoapatite Implants In Bone: Histology And Ultrastructure Of The Inerface", *J. Bio. Mat. Res.*, vol. 29:9–18, (1995).

Annals of NY Academy of Sciences, vol. 523, Jun. 10, 1988, "Mechanical And Bone Ingrowth–Properties Of A Polymer –Coated Porous Synthetic Coralline Hydroxyapatite Bone Graft Material", pp. 157–172, A. F. Tencer, P. L . . Woodard, J. Swenson and K. L. Brown.

Tian, Y., "A Novel Chondrocyte–Seeded Hydroxyapatite –Collagen Scaffold For Cartilage Repair", *Fifth World Biomaterials Congress*, (1996).

* cited by examiner

BONE SUBSTITUTES

This application is a Divisional of U.S. Ser. No. 08/944,006 filed Oct. 1, 1997 now U.S. Pat. No. 6,296,667.

FIELD OF THE INVENTION

The present invention relates in general to bone substitute materials, and particularly to porous materials capable of supporting or encouraging bone ingrowth into its pores.

BACKGROUND OF THE INVENTION

In the case of fracture or other injury to bone, proper bone healing and subsequent favorable bone remodeling is highly dependent on maintaining stability between bone fragments and, in the case of decalcified bone, on maintaining physiologic strain levels. External structural support can be gained using external braces, casts and the like. Internal structural support commonly is supplied by internal fixation devices such as bone plates, screws, intraredullar rods, etc., some of which may need to be surgically removed at a later time and all of which may prove to be burdensome and traumatic to a patient.

There is thus a need for a product that is a bone substitute product that is a bone graft material and that also provides structural support. This is especially so in the replacement or repair of long bones of the lower extremities and for use in spinal fusion techniques. Trauma, osteoporosis, severe osteo arthritis or rheumatoid arthritis, joint replacement, and bone cancers may call for treatment involving the use of structural bone substitute materials. A successful bone graft requires an osteoconductive matrix providing a scaffold for bone ingrowth, osteoinductive factors providing chemical agents that induce bone regeneration and repair, osteogenic cells providing the basic building blocks for bone regeneration by their ability to differentiate into osteoblasts and osteoclasts, and structural integrity provided to the graft site suitable for the loads to be carried by the graft.

Current bone graft materials include autografts (the use of bone from the patient), allografts (the use of cadaver bone), and a variety of artificial or synthetic bone substitute materials. Autografts grafts are comprised of cancellous bone and/or cortical bone. Cancellous bone grafts provide virtually no structural integrity. Bone strength increases as the graft incorporates and new bone is laid down. For cortical bone, the graft initially provides some structural strength. However, as the graft is incorporated by the host bone, nonviable bone is removed by resorption significantly reducing the strength of the graft. The use of autograft bone may result in severe patient pain at the harvest site, and there is of course a limit to the amount of such bone that can be harvested from the patient. Allografts are similar to autografts in that they are comprised of cancellous and/or cortical bone with greater quantities and sizes being available. Sterilization techniques for allografts may compromise the structural and biochemical properties of the graft. The use of allograft bone bears at least some risk of transfer of disease and the risk that the graft may not be well incorporated.

For structural bone repair materials to be conveniently used, they must be capable of being formed into complex shapes that are designed to fit the contours of the repair site. An accurately contoured graft will enhance the integration of natural bone and provide better load carrying capability. Intimate, load carrying contact often is required between the natural bone and the bone substitute material to promote bone remodeling and regeneration leading to incorporation of the graft by host bone. Ideally, the strength and stiffness and resilience (that is, its response to load and rate of load) of the bone substitute material should be similar to those of natural bone.

A general overview of orthopedic implantable materials is given in Damien, Christopher J., and Parsons, Russell J., "Bone Graft and Bone Graft Substitutes: A Review of Current Technology and Applications," Journal of Applied Biomaterials. Vol. 2. pp. 187–208 (1991).

A variety of materials have been proposed for use as bone substitute materials, ranging to from shaped porous metal objects suitable for defect filling around knee and hip joint replacements on the one hand to shaped ceramic materials on the other. Ceramic materials by and large have been formed through a sintering process in which a powder of a ceramic material such as zirconia is compressed to a desired shape in a mold and is then heated to sintering temperatures. The porosity of the resulting material is commonly quite low. Materials employing calcium phosphates (for example: fluorapatite, hydroxyapatite, and tricalcium phosphate) can also be sintered in this manner, the calcium phosphate having the capacity for acting as a substrate for bone growth (osteoconductivity).

It has been suggested to mix ceramic powders such as zirconia and hydroxyapatite, or fluorapatite and spinel, and then compress the mixture in a mold and either sinter or hot isostatically press to produce a somewhat porous ceramic of zirconia having pores at least partially filled with hydroxyapatite. Reference is made to Tamari et al., U.S. Pat. No. 4,957,509, and also Aksaci, D. et al., Porous Fluorapatite/spinel Osteoceramic for Bone Bridges, Ceramic Transactions, Vol. 48 p. 283 (1995). It has also been suggested to use ceramic articles having both high porosity and low porosity portions, and reference is made here to Hakamatsuka et al., U.S. Pat. No. 5,152,791, Johansson, U.S. Pat. No. 5,464,440 and Borom, U.S. Pat. No. 4,237,559. See also Klawitter et al. U.S. Pat. No. 4,000,525. The latter reference refers to the use of an $Al_2O_3$ slip that is foamed into a sponge, followed by firing.

By and large, metal or ceramic materials that have been proposed for bone substitutes have been of low porosity and have involved substantially dense metals and ceramics with semi-porous surfaces filled or coated with a calcium phosphate based material. The resulting structure has a dense metal or ceramic core and a surface which is a composite of the core material and a calcium phosphate, or a surface which is essentially a calcium phosphate. The bone substitute materials of this type commonly are heavy and dense, and often are significantly stiffer in structure than bone. Reference here is made to U.S. Pat. Nos. 5,306,673 (Hermansson et al.), 4,599,085 (Riess et al.), 4,626,392 (Kondo et al.), and 4,967,509 (Tamari et al.). Whereas natural bone, when stressed in compression, fails gradually (some components of the bone serving to distribute the load), bone substitute materials such as those described above commonly fail suddenly and catastrophically.

SUMMARY OF THE INVENTION

The present invention provides a strong composite article that is useful as a bone substitute material. The article comprises a supporting open skeleton or framework having interconnecting struts defining a plurality of interstices, the struts bearing a coating of a bioresorbable resilient material. Preferably, the article includes an osteoconductive material within the interstices and separated from the struts by the resilient material. The article may include materials that foster bone in-growth.

In one embodiment, the invention provides a strong article useful as a bone substitute material. The article comprises a continuous strong supportive framework having struts defining a plurality of interconnecting interstices throughout the bulk volume of the article, an osteoconductive material contained within the interstices, and a comparatively resilient interlayer which is bioresorbable and which is carried between and at least partially separates the supportive framework and the osteoconductive material. In response to physical stress imposed on the article, the interlayer serves to transmit and distribute loads within the article to including hydraulic stiffening of the struts, in a manner similar to the response of natural bone to applied stress. Failure of the article is not sudden and catastrophic but rather is gradual. In this embodiment, the invention may be thought of as providing a strong composite article that is useful as a bone substitute material, the article being comprised of a supporting open skeleton or framework in the corpus of which are osteoconductive materials that are incorporated by or surrounded by bioresorbable resilient materials. The article may include materials that foster bone in-growth.

The supportive framework preferably is of a ceramic material having struts defining a plurality of interconnecting interstices throughout the bulk volume of the article, and an osteoconductive composition carried by said supporting framework and exposed to-the interconnected openings. The osteoconductive composition occupies at least a portion of the same bulk volume as the framework component. Desirably, the supportive framework has void volumes that are in the range of 20% to 90% and preferably at least 50%. Further, the mean size of the openings of the supportive framework component desirably are at least 50 μm and preferably are in the range of 200 μm to 600 μm.

The polymeric material is a bioresorbable polymer which may be one or a combination of: collagen, poly-lactic acid, poly-glycolic acid, copolymers of lactic acid and glycolic acid, chitosan, chitin, gelatin, or any other resorbable polymer. This polymer material may be used alone, may be reinforced with a particulate or fibrous biocompatible material, and the composite may include a biological agent known to induce bone formation. This polymeric material will resorb as host bone grows into the interstices to replace it.

The osteoconductive composition, though it may also be a continuous interconnected body, is smaller in volume than the spaces in the framework interstices; thus there is a gap between it and the framework struts. This gap is filled with a bioresorbable resilient material so as to provide an energy absorbing interface that serves to provide load distribution and a hydraulic shock absorbing function. The osteoconductive composition may, instead, be added during a surgical procedure to the interstices of a supportive framework, the struts of which have been coated with a resilient material.

In a preferred embodiment, the supportive framework, the osteoconductive composition and the resilient, bioresorbable material each are continuous three dimensional structures that exhibit 3—3 connectivity and occupy at least a portion and preferably the entirety of the same bulk volume, each continuous structure having interconnected openings that interconnect with the openings of the other. Here, the resilient layer serves to transfer and distribute load from the supportive framework to the osteoconductive material, increasing the strength of the structure and tending to avoid brittle behavior under maximum material conditions. It is believed that the resulting article will transfer stress to the surrounding bone in a more physiologic way than does a dense ceramic or metal body. This stress transfer is important in stimulating bone growth and remodeling surrounding the graft, and avoiding "stress shielding," which is known to elicit an adverse bone remodeling response.

In yet another embodiment, the struts are comprised of a mixture or composite which contains the supportive material as well as osteoconductive material, the support material providing strength to the article and the osteoconductive material being carried at least partially on the surface of the interstices so as to be exposed to the interconnected openings to provide an osteoconductive environment favoring bone growth. The struts are coated with, or the interstices contain a bioresorbable, resilient material.

In a further embodiment, the supportive framework comprises struts that are coated with a bioresorbable resilient material to define interstices that open onto surfaces of the article and that can be filled with a calcium phosphate cement during a surgical procedure. In this embodiment, the calcium phosphate cement hardens within the interstices and the resilient material separating the supportive framework from the hardened calcium phosphate cement acts to cushion forces that are generated by exterior loads on the framework.

In yet another embodiment, the interstices of the strong framework are filled with a composite of a biocompatible, bioresorbable resilient material as a matrix containing particles of calcium phosphate or other osteoconductive material.

In yet a further embodiment, the invention comprises an open celled article of any of the several types described above and including a second substantially dense continuous material component attached to a surface of the bulk volume of the first material, the second component having a porosity not greater than 10% of its bulk volume. This substantially dense phase may be either a ceramic, a polymer, a metal, or a composite material.

DETAILED DESCRIPTION OF THE PREFERRED EMBODIMENT

In preparing articles of the invention, it is preferred to begin with the formation of a supportive, open framework having interstices in the size range of about 50 μm to about 1000 μm and preferably from about 200 μm to about 600 μm and having void volumes of at least about 30%, preferably at least about 50% and most preferably at least about 70%. The material of the framework may comprise any strong, hard, biologically-compatible material such as ceramic materials, metals and composites such as zirconia, zirconia/hydroxyapatite combinations, and zirconia toughened alumina. Preferably, the framework component is of a ceramic material, zirconia, alumina and calcium phosphates and combinations thereof being preferred.

In one preferred method, a slip of ceramic material is made by combining a ceramic powder such as zirconia with an organic binder and water to form a dispersion. The strut surfaces of an organic reticulated foam such as one of the various commercially available foams made of polyurethane, polyester, polyether, or the like are wetted and coated with the ceramic slip. The reticulated material may be immersed in the slip, and then removed and drained to remove excess slip. If desired, further excess slip can be removed by any of a variety of methods including passing the material between a pair of closely spaced rollers. By impacting the material with a jet of air, remaining slip that may fill the interstices by surface tension may be cleared. Varying the slip concentration, viscosity, and surface tension provides control over the amount of slip that is retained on the foam strut surfaces. Wetting agents and viscosity control agents also may be used for this purpose. A wide variety of reticulated, open cell materials can be employed, including natural and synthetic sponge materials and woven and non-woven materials, it being necessary in this embodiment only that the open cell material enables ceramic slip material to penetrate substantially fully through the openings in the structure.

Once the reticular struts are coated with slip, the slip solvent is removed by drying, accompanied desirably by mild heating, and the structure is then raised to sintering temperatures at which the ceramic particles at least partially sinter to form a rigid, light framework structure that mimics the configuration of the reticular struts. Before reaching sintering temperatures, the slip-treated sponge desirably is held at a temperature at which the organic material pyrolizes or burns away, leaving behind an incompletely sintered ceramic framework structure which then is raised to the appropriate sintering temperature.

Figure 1:
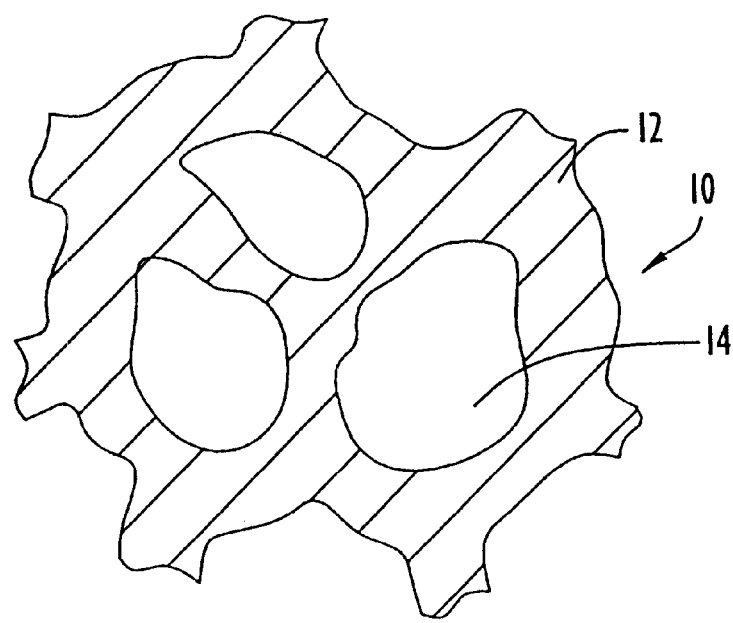
FIG. 1 is a broken-away, schematic drawing illustrating a ceramic framework useful in preparing articles of the invention.

Pyrolizing or oxidizing temperatures for most organics are in the range of about 200° C. to about 600° C. and sintering temperatures for most ceramics of relevance to this invention are in the range of about 1100° C. to about 1600° C. Zirconia and alumina or composites based on zirconia and alumina are the preferred ceramic materials for the structural elements unless the struts are also intended to be bioresorbable, in which case calcium phosphates can also be used. Examples of ceramic materials for the osteoconductive portion include calcium phosphates such as hydroxyapatite, fluorapatite, tricalcium phosphate and mixtures thereof, bioactive glasses, osteoconductive cements, and compositions containing calcium sulfate or calcium carbonate. A small, broken-away and highly magnified portion of the supporting framework is shown schematically in FIGS. 1 through 5 as 10, the framework having struts 12 defining open interstices 14 as shown in FIG. 1.

Metals which can be used to form the hard, strong, continuous framework component include titanium, stainless steels, cobalt/chrome alloys, tantalum, titanium-nickel alloys such as Nitinol and other superelastic metal alloys. Reference is made to Itin, et al., "Mechanical Properties and Shape Memory of Porous Nitinol," Materials Characterization [32] pp. 179–187 (1994); Bobyn, et al., "Bone Ingrowth Kinetics and Interface Mechanics of a Porous Tantalum Implant Material," Transactions of the 43rd Annual Meeting, Orthopaedic Research Society, p. 758, Feb. 9–13, 1997 San Francisco, Calif.; and to Pederson, et al., "Finite Element Characterization of a Porous Tantalum Material for Treatment of Avascular Necrosis," Transactions of the 43rd Annual Meeting, Orthopaedic Research Society, p. 598 Feb. 9–13, 1997. San Francisco, Calif., the teachings of all of which are incorporated by reference. Metals can be formed into hard, strong, continuous supportive frameworks by a variety of Aid manufacturing procedures including combustion synthesis, plating onto a "foam" substrate, chemical vapor deposition (see U.S. Pat. No. 5,282,861), lost mold techniques (see U.S. Pat. No. 3,616,841), foaming molten metal (see U.S. Pat. Nos. 5,281,251, 3,816,952 and 3,790,365) and replication of reticulated polymeric foams with a slurry of metal powder as described for ceramic powders.

The osteoconductive and osteoinductive materials that are appropriate for use in the present invention are biologically acceptable and include such osteoconductive materials as collagen and the various forms of calcium phosphates including hydroxyapatite; tricalcium phosphate; and fluorapatite, and such osteoinductive substances as: bone morphogenetic proteins (e.g.. rhBMP-2); demineralized bone matrix; transforming growth factors (e.g.. TGF-β); osteoblast cells, and various other organic species known to induce bone formation. The osteoconductive and osteoinductive properties may be provided by bone marrow, blood plasma, or morselized bone of the patient, or commercially available materials. Osteoinductive materials such as BMP may be applied to articles of the invention, for example, by immersing the article in an aqueous solution of this material in a dilute suspension of type I collagen. Osteoinductive materials such as TGF-β may be applied to an article of the invention from a saline solution containing an effective concentration of TGF-β, or may be carried in the resilient material.

The continuous supporting framework having interconnecting interstices or openings may be considered to be the primary load bearing element, and the osteoconductive material commonly is weaker than the supporting framework. The supporting framework is preferably formed, as mentioned above, of a ceramic material such as zirconia. The framework structure is formed such that the interstices or openings themselves, on average, are wider than are the thicknesses of the struts which separate neighboring interstices. The load bearing framework is essentially completely continuous and self interconnected in three dimensions, and the void portion is also essentially completely continuous and self interconnected in three dimensions. These two three dimensionally interconnected parts are intercolated with one another. This can be referred to as a 3—3 connectivity structure where the first number refers to the number of dimensions in which the load bearing framework is connected, and the second number refers to the number of dimensions in which the void portion is connected. The concept of connectivity is explained at greater length in Newnham et al. "Connectivity and Piezoelectric-Pyroelectric Composites," Materials Research Bulletin, Vol. 13 pp. 525–536 (1978), the teachings of which are incorporated herein by reference. With the supporting framework described herein, the framework itself is given a 3 as it is connected in 3 dimensions, and the void portion is treated likewise. In contrast, partially sintered assemblages of powders invariably contain isolated pores or voids which are not connected to all other voids. A material with all isolated (that is, dead end) pores in a dense matrix would have 3-0 connectivity. A material having pores that pass completely through the matrix in one dimension would yield 3-1 connectivity, and a material having pores that interconnect two perpendicular faces but not the third would have 3-2 connectivity.

In the preferred embodiment, the voids of the framework include a three-dimensional continuous network of an osteoconductive material such as a calcium phosphate, and also a three dimensional, continuous network of a resilient, desirably bioabsorbable material between the struts of the framework and the osteoconductive material, this configuration providing 3—3 connectivity.

The opening sizes in the supportive framework preferably are at least about 50 µm and preferably are on the order of 200 µm to about 600 µm. It is preferred that there be substantially no pores or voids less than 50 µm. It should be understood that the openings in the supportive framework are of myriad irregular shapes. The interconnected openings or interstices through which biological ingrowth processes can take place define in three dimensions a labyrinth in which bone ingrowth and vascularization can occur; that is, the openings have many junctures with other openings to thus define tortuous pathways through the framework. In general, it is believed that in order to adequately support the growth of bone into the framework openings, the openings must be capable of accommodating the passage of tissue having transverse dimensions of at least about 50 µm. Conceptually, it is convenient to think of a 50 µm opening in materials of the invention as being capable of accommodating the passage through it of a "worm" having a round cross section and a transverse diameter of 50 µm. Put another way, a 50 µm opening should enable passage through it of a sphere having a 50 µm diameter. Although there is no completely satisfactory way known to us for measuring the opening sizes, it is possible to examine a scanning electron micrograph of a cross section of an article of the invention and viewing it as a planar projection of the structure, drawing several lines across the micrograph, measuring the openings that intersected by the lines, and using averaging and standard deviation techniques to permit the size of the openings to be assessed.

Zirconia and other ceramics, when used to form the supportive framework, are exceedingly hard and are far more rigid than is bone. Although it would be desirable to employ as the supportive framework a material having a modulus of elasticity nearer to that of bone, bone substitute materials of the invention employing rigid materials work well. It is believed that the ultimate union of bone with such articles during the healing process occurs over a large surface area and depth as the encroaching bone penetrates into the bioabsorbable resilient material and the osteoconductive portions of the article. The substantial bone/ceramic interface that results enables forces to be readily transmitted to and from the ceramic framework with significantly less stress concentration in comparison to structure resulting from a bone/ceramic union that occurs within a small area of surface-to-surface contact and with little or no penetration of bone into the article.

When the osteoconductive material utilized is a ceramic, e.g., a calcium phosphate, and the supportive framework is a ceramic such as zirconia, several methods may be employed in the manufacture of the article of the invention. The supportive zirconia framework structure can be fabricated as indicated above, by coating a slip of zirconia on the surface of the struts of a reticulated organic material such as a foam of polyurethane, polyester, polyether or the like, and subsequently raising the temperature of the coated foam to drive off slip solvent, to pyrolize or burn off the organic foam material, and finally to heat the ceramic to cause the ceramic particles to at least partially sinter.

Figure 2:
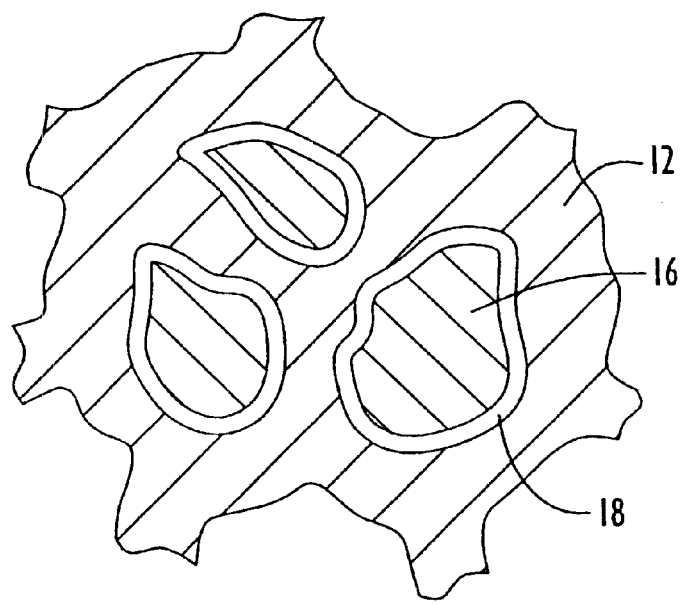
FIG. 2 is a broken-away, schematic drawing illustrating the ceramic framework of FIG. 1, the interstices of which include an osteoconductive material.

Once the ceramic framework has cooled, its interstices may be filled with a calcium phosphate utilizing an organic binder, and the resulting product may be sintered a second time, thus forming an included network of osteoconductive material within the interstices of the ceramic framework. As the calcium phosphate material is heated, it shrinks so as to form an intervening space between the struts forming the ceramic framework and the included calcium phosphate network. To ensure that the calcium phosphate material pulls away cleanly from the framework as it shrinks, the framework may first be lightly coated with a release agent such as paraffin. FIG. 2 depicts within the interstices of the supporting framework 12 the shrunken calcium phosphate material 16 and the space or gap 18 between the struts of the supporting framework and the calcium phosphate network.

Figure 3:
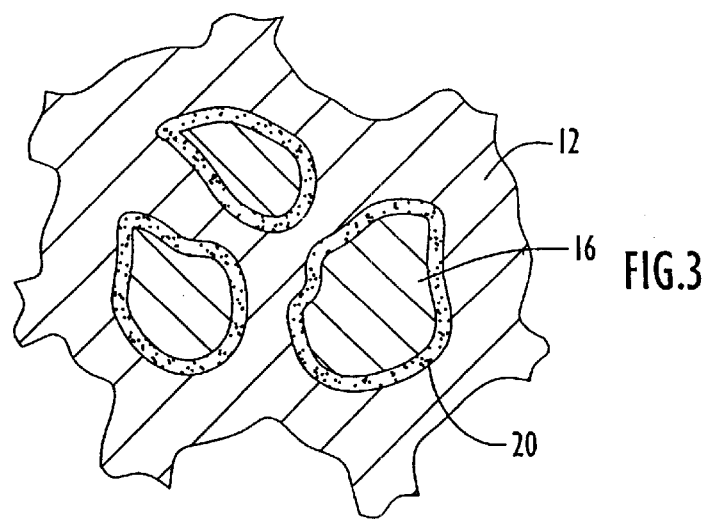
FIG. 3 is a broken-away, schematic drawing illustrating the ceramic framework of FIG. 2 showing a resilient material incorporated in the spaces between the ceramic framework and the osteoconductive material.
Figure 4:
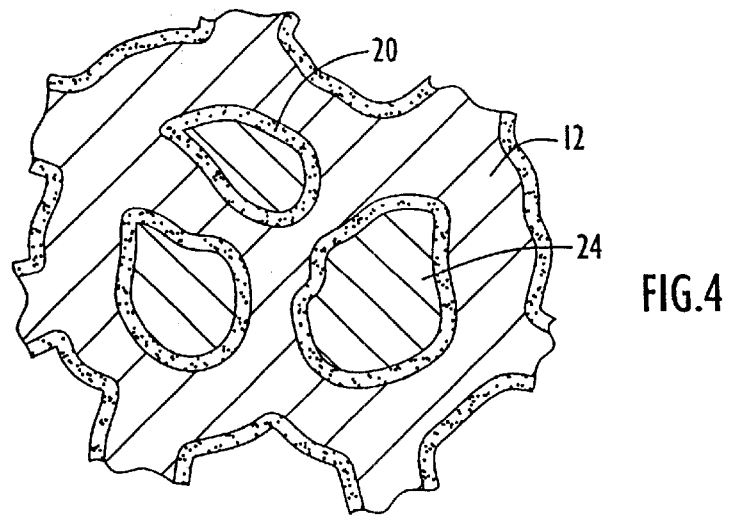
FIG. 4 is a broken-away, schematic drawing illustrating an embodiment of the invention.
Figure 5:
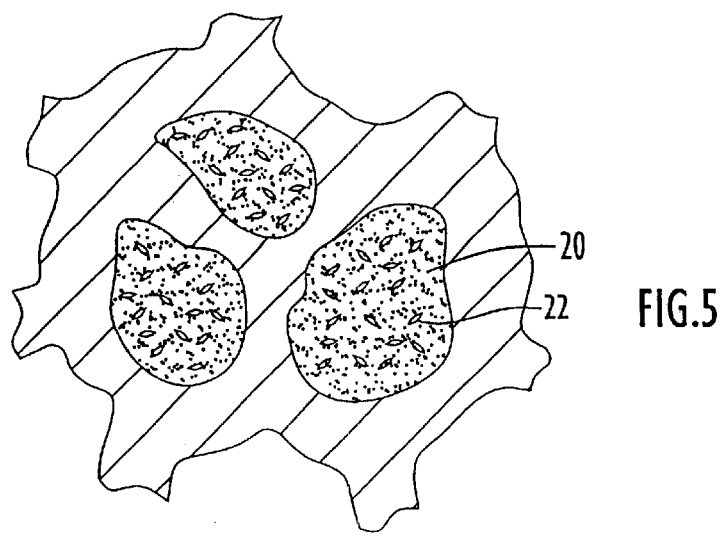
FIG. 5 is a broken-away, schematic drawing illustrating another embodiment of the invention.

The space 18 is then filled with a resilient, preferably bioresorbable material as described above. In this configuration, the supportive framework is continuous from one surface to the other, the included osteoconductive network is continuous and interconnecting and is coextensive with the interstices of the supportive framework Further, in some embodiments, the intervening resilient material also is continuous and coextensive with the framework and osteoconductive network. FIG. 3 depicts schematically the resilient interlayer 20 formed between the framework and the calcium phosphate network.

As referred to earlier, we may utilize the continuous, strong framework described above, e.g., of sintered zirconia, and form within the interstices of the framework a somewhat smaller structure of a second ceramic material such as calcium phosphate. Before adding a slip or paste of the second ceramic material to the completely formed and sintered supportive framework, the strut surfaces may be coated with a material such as wax to prevent the second ceramic material from bonding to the struts and to isolate the second ceramic material from the supportive framework. Since ceramic materials such as calcium phosphate shrink when they are sintered, the second material will occupy a space somewhat smaller than the space defined by the surrounding interstices of the supporting framework. The resulting spaces between the struts defining the interstices of the supporting framework and the calcium phosphate may be filled with a resilient biologically acceptable material such as a copolymer of glycolic acid and L-lactic acid. The resulting article, then, has a continuous strong supportive framework having struts defining a plurality of interconnecting interstices, a second framework carried within the interstices of the first framework, and a resilient interlayer between and separating the frameworks. The interlayer, it is believed, at least partially isolates the second framework from the first and, due to its resilient nature (in comparison to the relatively rigid first and second frameworks), serves to distribute internal loads between the frameworks.

Figure 6:
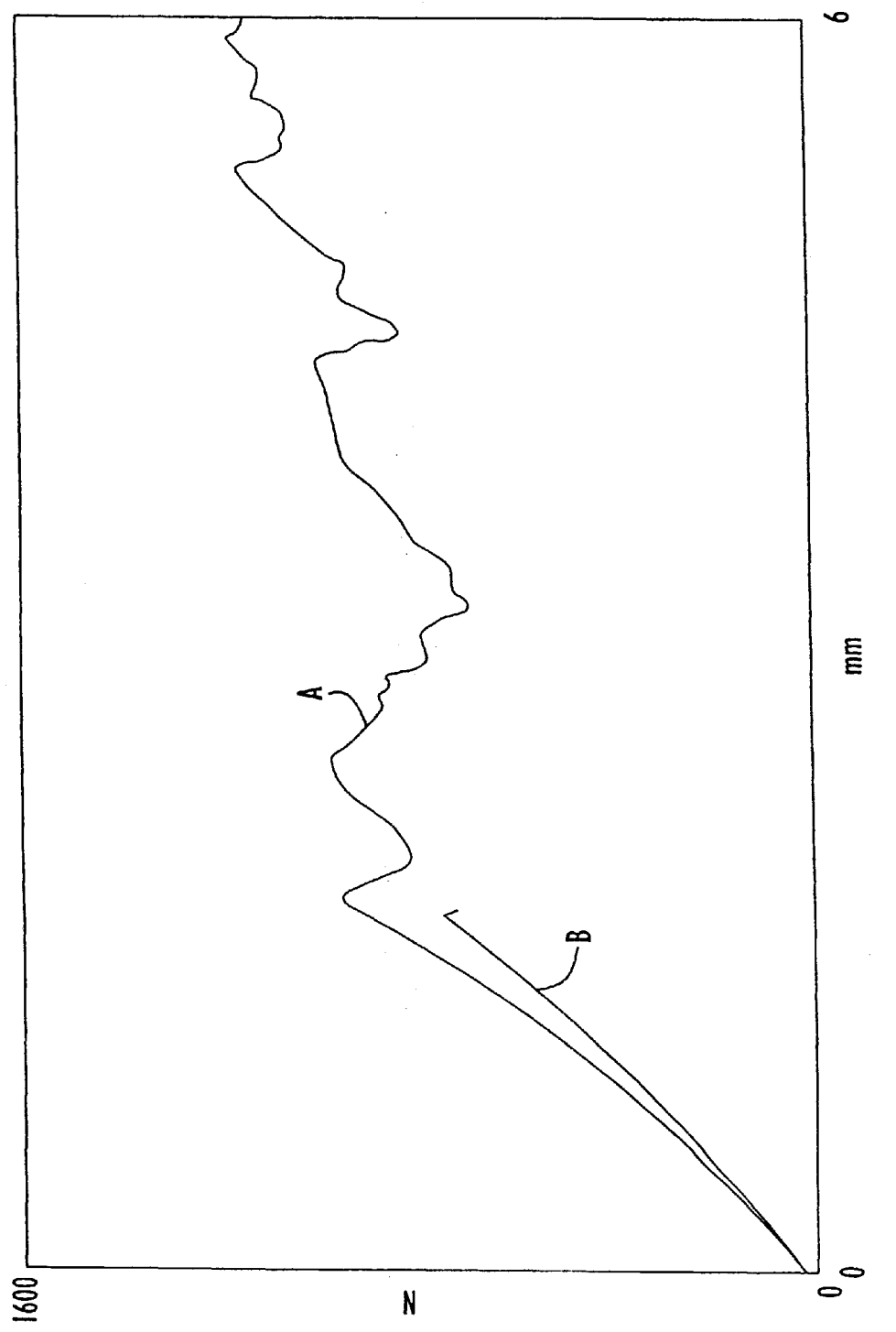
FIG. 6 is a graph of load versus strain illustrating the gradual failure mode of an article of the invention.

FIG. 6 illustrates a typical load-strain curve (curve A)resulting from compression testing of an article of the invention. The curve illustrates that the specimen did not fail catastrophically. Rather, the resilient interlayer enabled stresses within the specimen resulting from failure of portions of the framework to be distributed to other portions of the framework. Failure of the specimen was gradual, approximating the failure experienced when natural bone is similarly stressed. For purposes of comparison, curve B in FIG. 6 illustrates catastrophic failure of similar materials without resilient material present. The gradual failure mode is demonstrated also when struts are coated with resilient polymer, and there is no second framework.

Desirably, the supportive first framework is made of a strong material such as zirconia, and the second framework is of a material such as a calcium phosphate that provides osteoconductive properties, but where complete bioresorption is desired, the supportive first framework may also be a calcium phosphate composition.

When the framework component is of metal, the two-part system with interconnected pores can be formed in the same manner as when the framework component is of ceramic materials, that is, the osteoconductive material may be incorporated within the struts or may be formed within the interstices of the metal struts, or foamed within the interstices and sintered, followed by infusion of the resilient interface.

The "resilient" material referred to herein desirably is polymeric in nature and preferably is bioresorbable. By resilient, we refer to the ability of the material to be deformed when placed under stress without exhibiting brittle failure, the deformation tending to distribute stress within the article. The resilient material also serves to encase the struts during strut failure to provide residual compressive stiffness and to promote retention of physical integrity of the article. Preferably, the polymeric material is a bioresorbable polymer which may be one or a combination of: collagen, poly (lactic acid), poly (glycolic acid), copolymers of lactic acid and glycolic acid, chitin, chitosan, gelatin, or any other resorbable polymer. This polymer material may be used alone, may be reinforced with a particulate or fibrous biocompatible material, and may include one or more biological agents capable of inducing bone formation. Collagen and other polymeric materials may serve as suitable carriers of osteoinductive materials such as BMP and various bone growth proteins. Bioresorbable polymeric materials will resorb as host bone grows into the interstices to replace it.

In forming a framework that includes a coating, it may be desirable to heat the zirconia framework component to a temperature at which the liquid slip vehicle has substantially all been driven off and partial sintering has begun, this condition being referred to as a partially sintered stage. At this point, a hydroxyapatite slip or composite zirconia and hydroxyapatite slip may be applied, the slip solvent driven off with heat, and the zirconia and hydroxyapatite are raised to a sintering temperature and sintered together. The slip of calcium phosphate may have added to it viscosity control agents and a foaming agent such as hydrogen peroxide, or compressed gas. It may also have incorporated in it fibrous cellulosic materials. Upon introduction into the supportive zirconia framework structure of the hydroxyapatite slip, heating causes the slip to bubble and foam such that a number of smaller pores are formed in the calcium phosphate. Further heating will burn out the cellulosic materials, developing increased interconnectivity of the pores.

In another embodiment, the slip used to coat the polymeric reticulum and produce the ceramic reticulum contains fractions of both the supportive framework material (such as zirconia) and the osteoconductive material (such as calcium phosphate). The reticulated polymeric substrate is coated with slip and the excess is allowed to drain. Further excess slip is removed by passing the article through squeeze rollers or by impacting the article with compressed air. The resulting material is heated to drive off solvent, to pyrolyze the organic constituents, and to co-sinter the two components of the composite. In the zirconia-calcium phosphate system, the osteoconductive material (calcium phosphate) is preferably included in a range of 10 to 90 volume percent and preferably about 10 to 25 volume percent or 75 to 90 volume percent with respect to the total zirconia/calcium phosphate volume, sufficient osteoconductive material being used so as to provide an osteoconductive surface with respect to growing bone. Appropriate structures may use, for example, 25 volume percent of calcium phosphate and 75% of YSZ (yttria-stabilized zirconia). The reticulated article, that results has struts which are comprised of an intimate mixture of the two materials. The calcium phosphate may appear as very small islands on the surface of the zirconia strut. In any event, in this embodiment, the osteoconductive material remains exposed to the openings in the article so as to provide an osteoconductive effect with respect to encroaching bone. Of course, if desired, the supporting structure can be 100% osteoconductive material such as a calcium phosphate.

The bone substitute materials of the invention can be formed into the appropriate configurations for use as a bone substitute by several methods. In one preferred method, an organic material with open interstices such as a reticulated polyurethane foam is simply shaped to the desired configuration using ordinary cutting instruments such as scissors, scalpels, hot wire cutters and the like. The configured foam material is used in any of the foregoing methods to produce the article of the invention. In another method, an organic foam such as that referred to earlier is coated with a zirconia or other ceramic slip and is heated to drive off solvent and convert the ceramic to the "green" state, at which point it can be shaped into the desired configuration. In a further method, a bone substitute of the invention which has been fully sintered can be shaped by standard machining methods such as sawing and grinding, water jet or laser cutting, etc.

If the supporting framework of the article is of metal, it can be shaped through appropriate machining to the desired form before introducing an osteoconductive or osteoinductive material. It is contemplated that the pores of a metal material may be first filled with wax and the resulting structure frozen so that the wax supports the metal structure during machining, following which the wax is simply melted to enable the wax to escape. This procedure may have utility particularly when the metal framework component comprises a very thin walled- structure with large void openings, the struts of which, accordingly, can be unintentionally easily bent.

In a further embodiment, articles of the invention comprise a supporting framework with added resilient materials, the framework itself having relatively large openings and a high void volume and being attached, as by sintering to a second, denser structural element which may be of the same or different material but which has smaller openings and a smaller void volume. Preferably, this denser portion is substantially fully dense, that is, it has a void volume less than 10%. The denser portion may take the form a semitubular plate, a rod useful as a stem receivable in the intramedullary canal of a long bone for a total hip or knee replacement, or a plate useful as a tibial tray of a knee prosthesis, etc. The latter material may be formed in a thin layer relative to the first portion and the resulting structure mimics natural bone in that the second portion may be like cortical bone—the hard, dense, outer layer of a bone—whereas the first portion may be somewhat more open and porous and hence more closely resembles cancellous bone.

Figure 7:
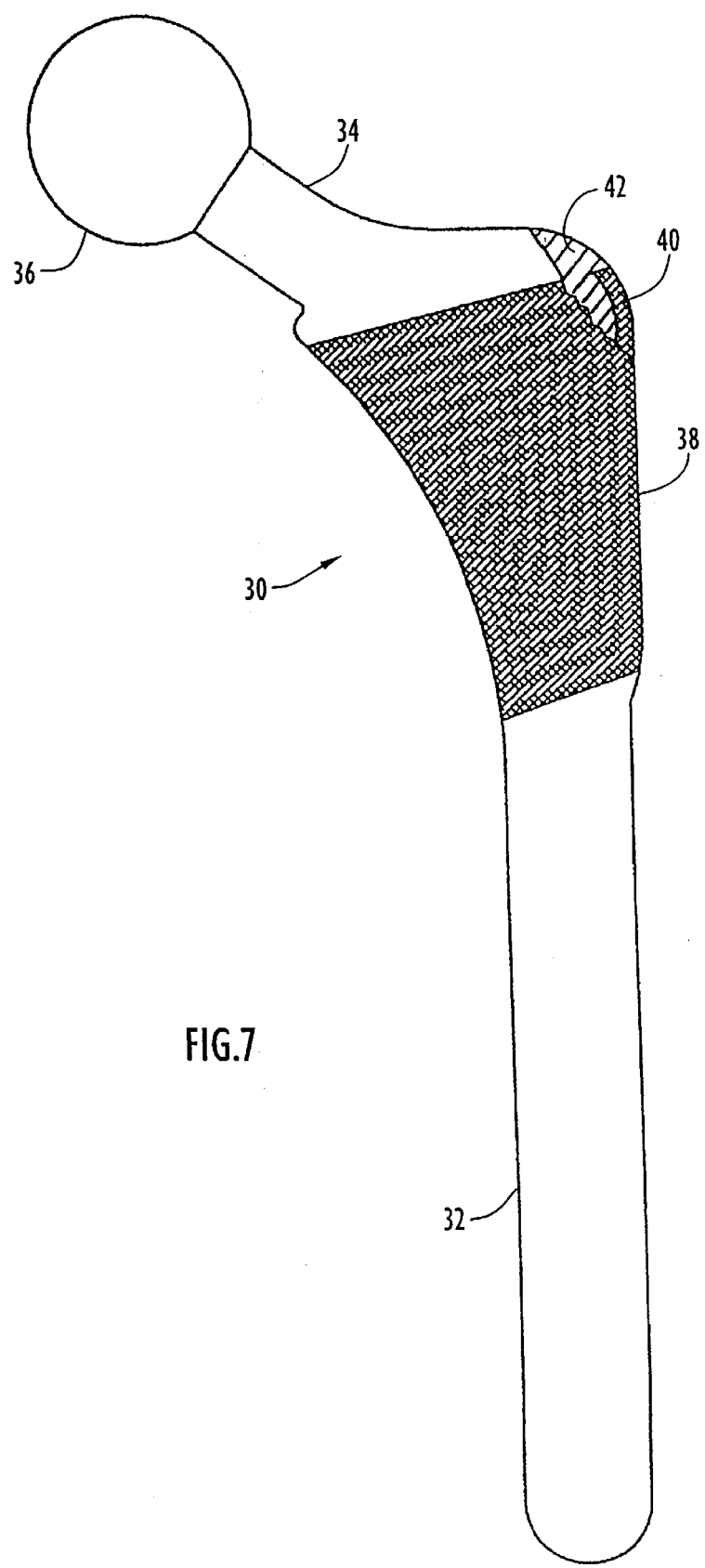
FIG. 7 is a broken away view of a femoral prosthesis utilizing an embodiment of the invention.

FIG. 7 shows a femoral hip stem prosthesis 30 made entirely of ceramic, the prosthesis having a dense stem portion 32, an angular neck 34 terminating in an articulating ball 36, and an angular shoulder portion 38. As shown in FIG. 7, the shoulder portion includes a thick layer 40 of an article of the invention having a framework with relatively large openings, carried by the denser portion 42 of the prosthesis. The coating 38 promotes bone ingrowth when the prosthesis has been implanted in the femur of a patent.

Figure 8:
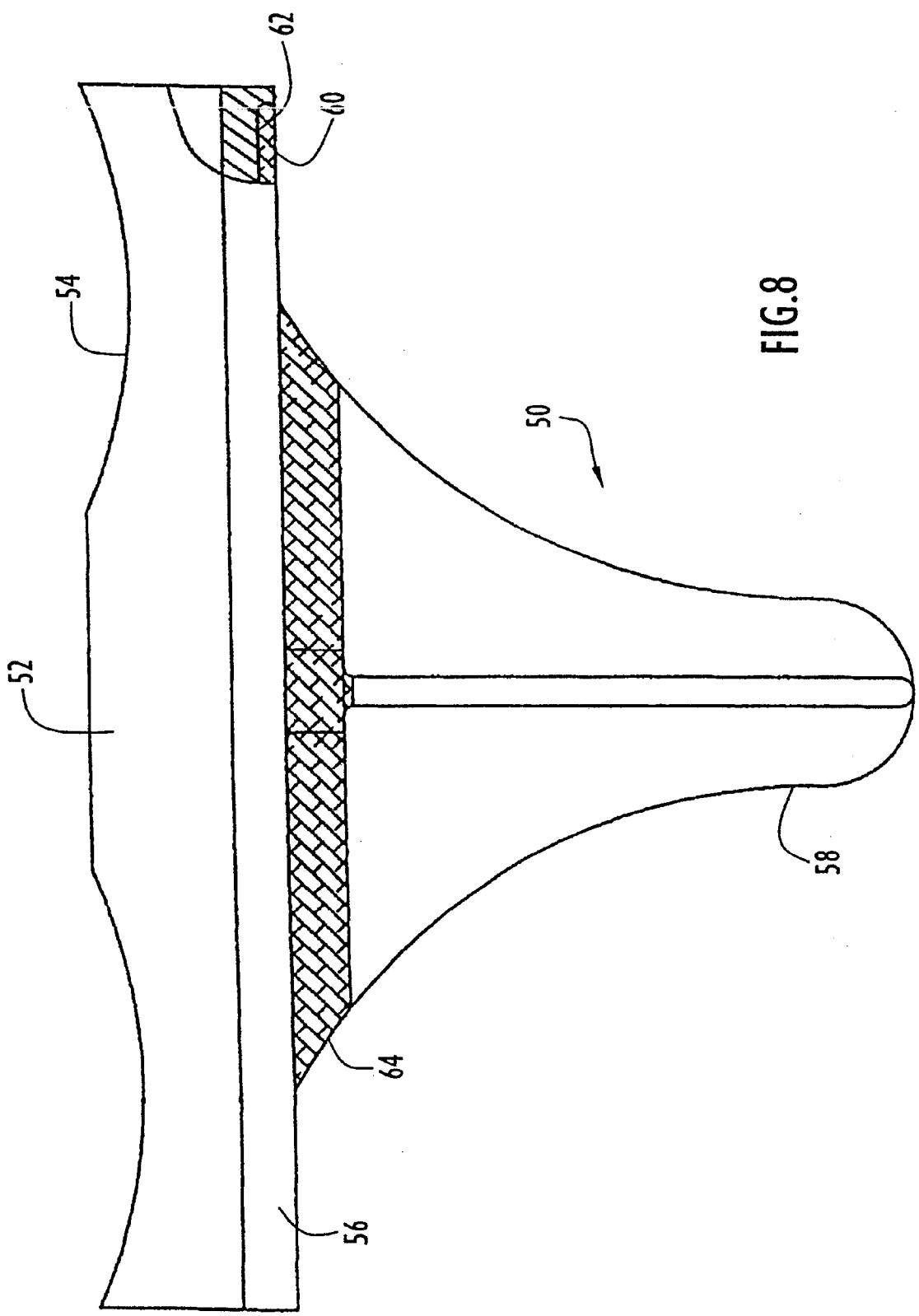
FIG. 8 is a broken away view of a tibial tray prosthesis utilizing an embodiment of the invention.

FIG. 8 depicts a tibial tray 50 having an upper plate 52 of ultra high molecular weight polyethylene having an articulating upper surface 54. The ultra high molecular weight polyethylene plate is supported by a plate 56 of the dense material of the invention, the plate 56 being integrally formed with a downwardly extending stem 58. The open framework material of the invention is shown in the form of a plate 60 which is received within a downwardly open recess 62 formed in the bottom of the plate 56, the framework 60 extending downwardly about the upper end of the stem, as shown at 64 in a relatively thick layer to promote bone ingrowth in this area.

The dense portion of this construct can be prepared by any of the common ceramic forming techniques such as slip casting, , tape casting, or coating and drying successive layers of slip onto a surface of a "foam" until a dense layer is formed. Dry pressing, injection molding and extrusion techniques may also be appropriate. The "green" dense portion is joined to the "green" low density portion through the use of a ceramic slip of substantially similar composition to the slip used in the formation of the low density portion or of a substantially similar composition to the slip used in the formation of the dense portion in the case of slip cast dense portion. "Green" here refers to the state of a ceramic article which has been formed and dried to a self-supporting structure but from which the organic constituents have not yet been removed. The dense portion may be alternatively comprised of a resorbable polymeric material, a resorbable ceramic material, or a resorbable composite material in addition to materials enumerated above.

The above description has centered upon completely formed bone substitute articles having a supporting, open framework, an osteoconductive material generally coextensive with and contained within the supporting framework, and a resilient, preferably bioresorbable polymer between the supporting framework and the osteoconductive material. If desired, the osteoconductive material need not be continuous within the interstices of the supporting framework. Here, the osteoconductive material may instead be particulate, as shown at 22 in FIG. 5, and may be carried by or embedded in the resilient material 20. In addition, the invention also relates to the embodiment illustrated in FIG. 4 in which the interstices of the supportive framework as described above, the interstices of which are coated with a resilient, desirably bioresorbable material, the coated interstices 24 opening onto surfaces of the article. With this embodiment, the coated interstices may be filled with a calcium phosphate cement during a surgical procedure. The calcium phosphate cement hardens within the interstices and the resilient material separating the supportive framework from the hardened calcium phosphate cement acts to distribute forces that are generated by exterior loads on the framework. The supporting open framework may alternatively be coated with resilient material with the interstices not being filled.

The invention may be more easily understood by reference to the following non-limiting examples:

EXAMPLE 1

A zirconia slip may be prepared by combining the following ingredients and mixing them thoroughly by ball milling in a polyethylene container using zirconia media:

150 grams partially stabilized zirconia powder (Zirconia Sales America)

2.25 grams dispersant (Rohm and Haas, product D-3021)

15 grams binder (Rohm and Haas product designation B-1000)

0.375 grams surfactant/wetting agent (Air Products Surfynol™ TG)

0.26 grams anti-foaming agent (Henkel NopCo™ NXZ)

36 ml deionized water

Pieces of reticulated polyester-polyurethane foam 10–80 pores per inch (Stephenson and Lawyer) are immersed in the above slip and repeatedly compressed to remove air bubbles trapped inside. The foams are removed from the slip and the excess slip is allowed to drain. Further excess slip is removed by passing the foams between a pair of stainless steel squeeze rollers several times. Passages are also cleared by blowing air through them. The resulting pieces are allowed to dry at room temperature followed by drying at temperatures up to 100° C. in air. When the pieces appear dry, they are heated to pyrolyze and remove organics (binder, dispersant, surfactant, anti-foam agent, and reticulated polymer foam) and then are sintered at a temperature of about 1400° C. for one hour. The preferred thermal cycle for the above involves raising the temperature of the pieces at the rate of 2° C. per minute to 600° C., holding the temperature at 600° C. for two hours, and then raising the temperature at the rate of 5° C. per minute to 1400° C., with a one hour hold at this temperature. The furnace is then cooled to room temperature at a rate of about 10° C. per minute. The resulting product is a strong, light weight, porous zirconia framework or reticulum of zirconia having a void volume of about 76%.

The framework is then dipped in molten paraffin wax and completely drained so as to leave a thin wax coating on the struts of the framework. An injectable calcium phosphate paste is made by combining and mixing the following:

| | |
|---|---|
| 29 grams | calcium phosphate (powder) |
| 3.5 grams | polyethylene oxide binder |
| 2 grams | dispersant (Darvan ™ C, R. T. Vanderbilt) |
| 3 drops | thickening agent (Rohm and Haas T-5000) |
| 2 drops | anti-foaming agent (Henkel Nopco ™ NXZ) |
| 30 ml | deionized water |

The paste is injected into the interstices of the zirconia framework and allowed to dry at 60° C. in air. The article is then sintered in nitrogen to 1300° C. for 1 hour. The resulting product has two intertwined networks of zirconia and calcium phosphate with a space at their interface.

A gel of collagen, type I, is made by mixing 20 parts of 50 mM acetic acid with 1 part collagen and stir blending. To this is added an equal volume of 4% chitosan solution in dilute acetic acid. This mixture is forced under pressure into the space between the intertwined networks, and upon drying forms a collagen /chitosan resilient interlayer between these networks.

EXAMPLE II

Example I is repeated except that the interface space is filled with a thin paste of a copolymer of glycolic acid and lactic acid (Alkermes "Medisorb" 85/15 PGA/PLLA) in ethyl acetate, mixed with an equal volume of collagen gel referred to in example I. The solvent is allowed to evaporate to form a resilient interlayer between these networks.

Depending on the concentration of the solution, this process may be repeated to build the polymer interface.

The resulting article was subjected to compressive stress testing and provided a force-displacement curve shown as A in FIG. 6. Curve B in FIG. 6 illustrates the brittle failure of the same product without the addition of the resilient interlayer.

EXAMPLE III

A zirconia framework is made as in Example I without the subsequent wax coating. The interstices are filled with a paste made of a suspension of Type 1 collagen in 50 mM acetic acid in a ratio of 1 part collagen to 20 parts acid in which calcium deficient hydroxyapatite crystals are grown (according to a process described by TenHuisen et al., J. Biomed. Materials Res. Vol. 29, pp. 803–810 (1995), which is incorporated herein by reference) from precursors tetracalcium phosphate ($CA_4(PO_4)_2O$ and monetite ($CaHPO_4$), to provide an article similar to that illustrated in FIG. 5.

EXAMPLE IV

A zirconia/hydroxyapatite composite framework was made as in Example 1 with 25 volume percent hydroxyapatite without the subsequent wax coating. The struts were coated with the solution of a copolymer of glycolic acid and lactic acid(Alkermes "Medisorb 75/25 PLLA/PGA) to provide a coating approximately 15 mils in thickness.

The interstices of the article are injected with calcium phosphate cement paste such as made by a process (described by Constantz, et al. SCIENCE, Vol. 267 (1995), the teachings of which are incorporated herein by reference), the paste comprising a mixture of monocalcium phosphate monohydrate, calcium phosphate and calcium carbonate in a sodium phosphate solution. The hardened paste provides a biomaterial suitable for implants that is now strengthened by the skeleton framework with its resilient interface.

EXAMPLE V

A calcium phosphate framework was made by coating a reticulated polyester-polyurethane foam with a slip of calcium phosphate as described in Example I. The resulting pieces were dried at up to 100° C. in air. Following drying the pieces were heated to pyrolyze and remove organics and were sintered at a temperature of about 1300° C. in nitrogen for one hour. The resulting calcium phosphate framework was then coated with a solution of a copolymer of lactic acid and glycolic acid(Alkermes "Medisorb 75/25 PLLA/PGA) in methylene chloride. The solvent was removed by vacuum.

EXAMPLE VI

A supportive framework was made as in Example I but utilizing a slip of zirconia and hydroxyapatite. The struts were coated, and the interstices partially filled with a solution of a copolymer of glycolic and lactic acid in methylene chloride. Following coating, the solvent was removed by vacuum.

EXAMPLE VII

The "green" ceramic reticulum formed as in Example I before sintering was wetted with a slip containing zirconia of the same composition, binders and zirconia powders, and was adhered to a green zirconia ceramic of the same composition made by a conventional ceramic slip casting process by sintering, the latter material simulating curved cortical bone and the reticulum simulating attached cancellous bone. The struts of the reticular portion are then coated with a copolymer of glycolic acid and lactic acid as in example II.

While a preferred embodiment of the present invention has been described, it should be understood that various changes, adaptation and modification may be made therein without departing from the spirit of the invention and the scope of the appended claims.

What is claimed is:

1. A method for producing a strong, porous article useful as a bone substitute material comprising a continuous strong supportive sintered, load-bearing framework having struts defining a plurality of interconnecting interstices having 3—3 connectivity, and a resilient coating within said interstices and encasing said struts to provide residual strength to the struts and retain mechanical integrity of the article upon strut failure, wherein said resilient coating comprises a bioresorbable polymer and wherein said method comprises, providing the continuous strong supportive sintered, load-bearing framework having struts defining a plurality of interconnecting interstices having 3—3 connectivity; and contacting the framework with the bioresorbable polymer whereby said struts are encased with the bioresorbable polymer.

2. A method according to claim 1, wherein the sintered, load-bearing framework comprises a composite of zirconia and calcium phosphate.

3. A method according to claim 1, wherein the sintered, load-bearing framework comprises a ceramic.

4. A method according to claim 3, wherein the sintered, load-bearing framework comprises one or more of alumina and zirconia.

5. A method according to claim 1, wherein the sintered, load-bearing framework comprises a metal.

6. A method according to claim 5, wherein the sintered, load-bearing framework comprises stainless steel.

7. A method according to claim 1, wherein the bioresorbable polymer comprises a polymer selected from the group consisting of collagen, chitosan, chitin, poly(glycolic acid), poly (lactic acid), a copolymer of glycolic and lactic acid and mixtures thereof.

8. A method according to claim 1, wherein the bioresorbable polymer comprises a polymer selected from the group consisting of collagen, chitosan, chitin and mixtures thereof.

9. A method according to claim 1, wherein the step of providing the continuous strong supportive sintered, load-bearing framework further comprises:

providing a reticulated foam;

providing a slip of a ceramic or metal;

contacting the reticulated foam with the slip;

removing any excess slip;

drying to remove slip solvent; and heating to a temperature sufficient to remove the reticulated foam and to sinter the framework.

10. A method according to claim 1, wherein the step of contacting the framework with the bioresorbable polymer further comprises coating the bioresorbable polymer on the struts of the framework.

11. A method according to claim 10, wherein the step of coating the bioresorbable polymer on the struts of the framework completely fills the interconnecting interstices.

12. A method according to claim 11, wherein the bioresorbable polymer includes a particulate osteoconductive material.

13. A method according to claim 1, wherein the interconnecting interstices have an opening ranging from 50 to 1000 μm.

14. A method according to claim 1, wherein the interconnecting interstices have an opening ranging from 200 to 600 μm.

15. A method of producing a strong, porous article useful as a bone substitute material comprising a continuous strong supportive sintered, load-bearing framework having struts defining a plurality of interconnecting interstices having 3—3 connectivity, a resilient coating within said interstices and encasing said struts to provide residual strength to the struts and retain mechanical integrity of the article upon strut failure, and an osteoconductive material contained within said interstices but separated from said struts by the resilient coating encasing said struts, wherein said method comprises, comprising:

providing a reticulated foam;
providing a slip of a ceramic or metal;
contacting the reticulated foam with the slip;
removing any excess slip;
drying to remove slip solvent; and
heating to a temperature sufficient to remove the reticulate foam and to sinter the framework to provide the continuous strong supportive sintered, load-bearing first framework having struts defining a plurality of interconnecting interstices;
providing within said interstices but spaced apart from said struts a solid osteoconductive material; and
providing a resilient interlayer between and at least partially separating said framework and said solid osteoconductive material.

16. A method as claimed in claim 15, wherein the step providing the osteoconductive material comprises:

providing a second rigid framework of an osteoconductive material contained within said interstices but spaced from said struts, and
the step of providing a resilient material comprises providing said resilient interlayer between and at least partially separating said first and second frameworks.

17. A method as claimed in claim 16, wherein the step of providing the osteoconductive material further comprises:

filling interstices of the sintered, load-bearing first framework with an osteoconductive material containing an organic binder; and
heating the osteoconductive material, whereby the osteoconductive material shrinks and forms an intervening space between the struts forming the first framework and the osteoconductive material second framework.

18. A method as claimed in claim 17, wherein the step of providing the osteoconductive material further comprises coating the struts of the first framework with a release agent before filling the interstices with the osteoconductive material.

19. A method as claimed in claim 18, wherein the release agent comprises a wax.

20. A method according to claim 15, wherein the sintered, load-bearing framework comprises a composite of zirconia and calcium phosphate.

21. A method according to claim 15, wherein the sintered, load-bearing framework comprises a ceramic.

22. A method according to claim 21, wherein the sintered, load-bearing framework comprises one or more of alumina and zirconia.

23. A method according to claim 15, wherein the bioresorbable polymer comprises a polymer selected from the group consisting of collagen, chistosan, chitin, poly(glycolic acid), poly (lactic acid), a copolymer of glycolic and lactic acid and mixtures thereof.

24. A method according to claim 15, wherein the interconnecting interstices have an opening ranging from 50 to 1000 μm.

25. A method according to claim 15, wherein the interconnecting interstices have an opening ranging from 200 to 600 μm.

26. A method of producing a strong, porous article useful as a bone substitute material comprising a continuous strong supportive sintered, load-bearing framework having struts defining a plurality of interconnecting interstices, an osteoconductive material contained within said interstices but separate from said struts, and a resilient material that completely fills the spaces between the struts and the osteoconductive material to provide residual strength to the struts and osteoconductive material retain mechanical integrity of the article upon strut failure, wherein the osteoconductive material is a continuous interconnected body, and wherein said method comprises:

providing a continuous strong supportive sintered load-bearing framework having struts defining a plurality of interconnecting interstices;
providing within said interstices but spaced from said struts, a solid osteoconductive material; and
providing a resilient interlayer between and at least partially separating said framework and said solid osteoconductive material.

27. A method according to claim 26, wherein the sintered, load-bearing framework comprises a composite of zirconia and calcium phosphate.

28. A method according to claim 26, wherein the sintered, load-bearing framework comprises a ceramic.

29. A method according to claim 28, wherein the sintered, load-bearing framework comprises one or more of alumina and zirconia.

30. A method according to claim 26, wherein the bioresorbable polymer comprises a polymer selected from the group consisting of collagen, chitosan, chitin, poly(glycolic acid), poly (lactic acid), a copolymer of glycolic and lactic acid and mixtures thereof.

31. A method according to claim 26, wherein the interconnecting interstices have an opening ranging from 50 to 1000 μm.

32. A method according to claim 26, wherein the interconnecting interstices have an opening ranging from 200 to 600 μm.

33. A method of producing a strong, porous article useful as a bone substitute material comprising a continuous strong supportive sintered, load-bearing ceramic framework having struts defining a plurality of interconnecting interstices having 3—3 connectivity wherein said method comprises:

providing a reticulated foam;
providing a slip of a ceramic or metal;
contacting the reticulated foam with the slip;
removing any excess slip;
drying to remove slip solvent; and
heating to a temperature sufficient to remove the reticulated foam and to sinter the framework.

34. A method according to claim 33, wherein the sintered, load-bearing ceramic framework comprises one or more of alumina, zirconia and calcium phosphate.

35. A strong, porous article useful as a bone substitute material comprising a continuous strong supportive sintered, load-bearing ceramic framework having struts defining a plurality of interconnecting interstices having 3—3 connectivity.

36. An article according to claim 35, wherein the sintered, load-bearing ceramic framework comprises one or more of alumina, zirconia and calcium phosphate.

* * * * *